US010828534B2

United States Patent
Cei et al.

(10) Patent No.: US 10,828,534 B2
(45) Date of Patent: Nov. 10, 2020

(54) METHOD OF ADAPTIVE CONTROL OF A TREADMILL, TREADMILL WITH ADAPTIVE CONTROL AND RELATED PROGRAM PRODUCT

(71) Applicant: TECHNOGYM S.p.A., Forli'-Cesena (IT)

(72) Inventors: Daniele Cei, Forli'-Cesena (IT); Alessandro Del Monaco, Forli'-Cesena (IT); Claudio Serra, Forli'-Cesena (IT)

(73) Assignee: TECHNOGYM S.p.A., Forli'-Cesena (IT)

( * ) Notice: Subject to any disclaimer, the term of this patent is extended or adjusted under 35 U.S.C. 154(b) by 155 days.

(21) Appl. No.: 15/787,383

(22) Filed: Oct. 18, 2017

(65) Prior Publication Data
US 2018/0111023 A1 Apr. 26, 2018

(30) Foreign Application Priority Data
Oct. 21, 2016 (IT) .......................... 102016000106425

(51) Int. Cl.
*A63B 24/00* (2006.01)
*G06F 19/00* (2018.01)
(Continued)

(52) U.S. Cl.
CPC ........ *A63B 24/0087* (2013.01); *A63B 22/025* (2015.10); *A63B 22/0242* (2013.01);
(Continued)

(58) Field of Classification Search
CPC .............. A63B 22/0242; A63B 22/025; A63B 22/0285; A63B 24/0062; A63B 24/0087;
(Continued)

(56) References Cited

U.S. PATENT DOCUMENTS 5,368,532 A * 11/1994 Farnet .................... A63B 22/02 482/5
5,476,430 A * 12/1995 Lee ........................ A63B 22/02 482/3
(Continued)

OTHER PUBLICATIONS

Italian Search Report for corresponding Italian Patent Application No. 102016000106425 dated Jun. 26, 2017, 7 pages.

*Primary Examiner* — Joshua Lee
(74) *Attorney, Agent, or Firm* — Merchant & Gould P.C.

(57) ABSTRACT

A method of adaptive control of a treadmill, the treadmill includes a base extending along a longitudinal axis, the base includes a first rotatable element and a second rotatable element adapted to rotate about respective rotation axes transversal to the longitudinal axis of the base. A physical exercise area operatively connects to the first and second rotatable elements. A motor is operatively associated with the first and/or second rotatable element. The motor is configured for rotating the first and the second rotatable and dragging in rotation the physical exercise surface. The method includes: determining by a data processing unit of the treadmill, a first electrical parameter of the treadmill representative of the interaction between a user and the physical exercise surface of the treadmill. The data processing unit controls the motor based on the first electrical parameter detected by the data processing unit.

9 Claims, 3 Drawing Sheets

(51) Int. Cl.
*G09B 19/00* (2006.01)
*H02P 29/40* (2016.01)
*A63B 22/02* (2006.01)

(52) U.S. Cl.
CPC ...... *A63B 22/0285* (2013.01); *A63B 24/0062* (2013.01); *G06F 19/3481* (2013.01); *G09B 19/0038* (2013.01); *H02P 29/40* (2016.02); *A63B 2024/0009* (2013.01); *A63B 2024/0093* (2013.01); *A63B 2220/30* (2013.01); *A63B 2220/31* (2013.01); *A63B 2220/36* (2013.01); *A63B 2220/40* (2013.01); *A63B 2220/56* (2013.01); *A63B 2220/803* (2013.01); *A63B 2220/833* (2013.01); *A63B 2225/50* (2013.01)

(58) Field of Classification Search
CPC .... A63B 2024/0009; A63B 2024/0093; A63B 2220/30; A63B 2220/31; A63B 2220/36; A63B 2220/40; A63B 2220/56; A63B 2220/803; A63B 2220/833; A63B 2225/50; G06F 19/3481; G09B 19/0038; H02P 29/40
See application file for complete search history.

(56) References Cited

U.S. PATENT DOCUMENTS

| | | | | |
|---|---|---|---|---|
| 5,707,319 A * | 1/1998 | Riley | .................. | A63B 22/001 482/54 |
| 5,800,314 A * | 9/1998 | Sakakibara | ............ | A63B 22/02 482/1 |
| 5,856,736 A * | 1/1999 | Rotunda | ........... | H02M 7/53875 318/802 |
| 6,179,754 B1 * | 1/2001 | Wang | .................. | A63B 22/0242 482/21 |
| 6,283,896 B1 * | 9/2001 | Grunfeld | ................ | A63B 22/02 482/54 |
| 6,645,126 B1 * | 11/2003 | Martin | ............... | A63B 69/0059 482/3 |
| 7,094,180 B2 * | 8/2006 | Huang | .................. | A63B 22/02 482/51 |
| 7,101,319 B1 * | 9/2006 | Potts | .................. | A63B 22/0257 482/51 |
| 7,914,420 B2 * | 3/2011 | Daly | .................. | A63B 22/0235 119/700 |
| 8,480,541 B1 * | 7/2013 | Brunts | ............... | A63B 22/0242 482/1 |
| 9,517,378 B2 * | 12/2016 | Ashby | ................ | A63B 22/0242 |
| 10,258,828 B2 * | 4/2019 | Dalebout | ........... | A63B 24/0087 |
| 2005/0227820 A1 * | 10/2005 | Dyer | .................. | A63B 22/0023 482/54 |
| 2006/0009333 A1 * | 1/2006 | Wang | .................. | A63B 22/0242 482/54 |
| 2008/0182727 A1 | 7/2008 | Uang | | |
| 2009/0023556 A1 | 1/2009 | Daly et al. | | |
| 2009/0036272 A1 * | 2/2009 | Yoo | .................... | A63B 22/0257 482/7 |
| 2009/0270227 A1 * | 10/2009 | Ashby | ................ | A63B 22/0023 482/8 |
| 2010/0248900 A1 * | 9/2010 | Ashby | .................... | A63B 22/02 482/4 |
| 2012/0040798 A1 * | 2/2012 | Yu | ...................... | A63B 22/0242 482/4 |
| 2012/0237911 A1 * | 9/2012 | Watterson | .......... | A63B 24/0087 434/247 |
| 2013/0274069 A1 * | 10/2013 | Watterson | .......... | A63B 24/0087 482/9 |
| 2016/0296800 A1 * | 10/2016 | Devor | ............... | A63B 24/0087 |
| 2017/0065851 A1 * | 3/2017 | Deluca | ............... | A63B 24/0087 |

\* cited by examiner

METHOD OF ADAPTIVE CONTROL OF A TREADMILL, TREADMILL WITH ADAPTIVE CONTROL AND RELATED PROGRAM PRODUCT

This application claims benefit of Serial No. 102016000106425, filed 21 Oct. 2016 in Italy and which application is incorporated herein by reference. To the extent appropriate, a claim of priority is made to each of the above disclosed applications.

BACKGROUND OF THE INVENTION

The present disclosure relates to the fitness sector, and in particular to a method of adaptive control of a treadmill, to a treadmill with adaptive control and to a related program product.

As known, a treadmill is now a common exercise machine which can be employed by an user for physical activities (running, walking and thrusting exercises, and so on) for normal training and for physical rehabilitation purposes.

Nowadays, the need is strongly felt to control the treadmill adaptively in order to be able to allow the user to perform the physical activity on the treadmill in the most natural and high performing manner possible.

From this point of view, the most common treadmills, which envisage the initial setting of a constant advancement speed of the belt, show a major limit.

SUMMARY OF THE INVENTION

It is the object of the present disclosure to devise and provide a method of adaptive control of a treadmill which allows avoiding at least partially the drawback described above with reference to the prior art.

It is the object of the present disclosure also a treadmill with adaptive control and a related program product.

BRIEF DESCRIPTION OF THE DRAWINGS

Further features and advantages of the method of adaptive control of a treadmill, of the treadmill with adaptive control and of the related program product according to the present disclosure will be apparent from the following description indicatively provided by way of non-limiting example with reference to the accompanying figures, in which.

DETAILED DESCRIPTION OF THE PREFERRED EMBODIMENTS

Figure 1:
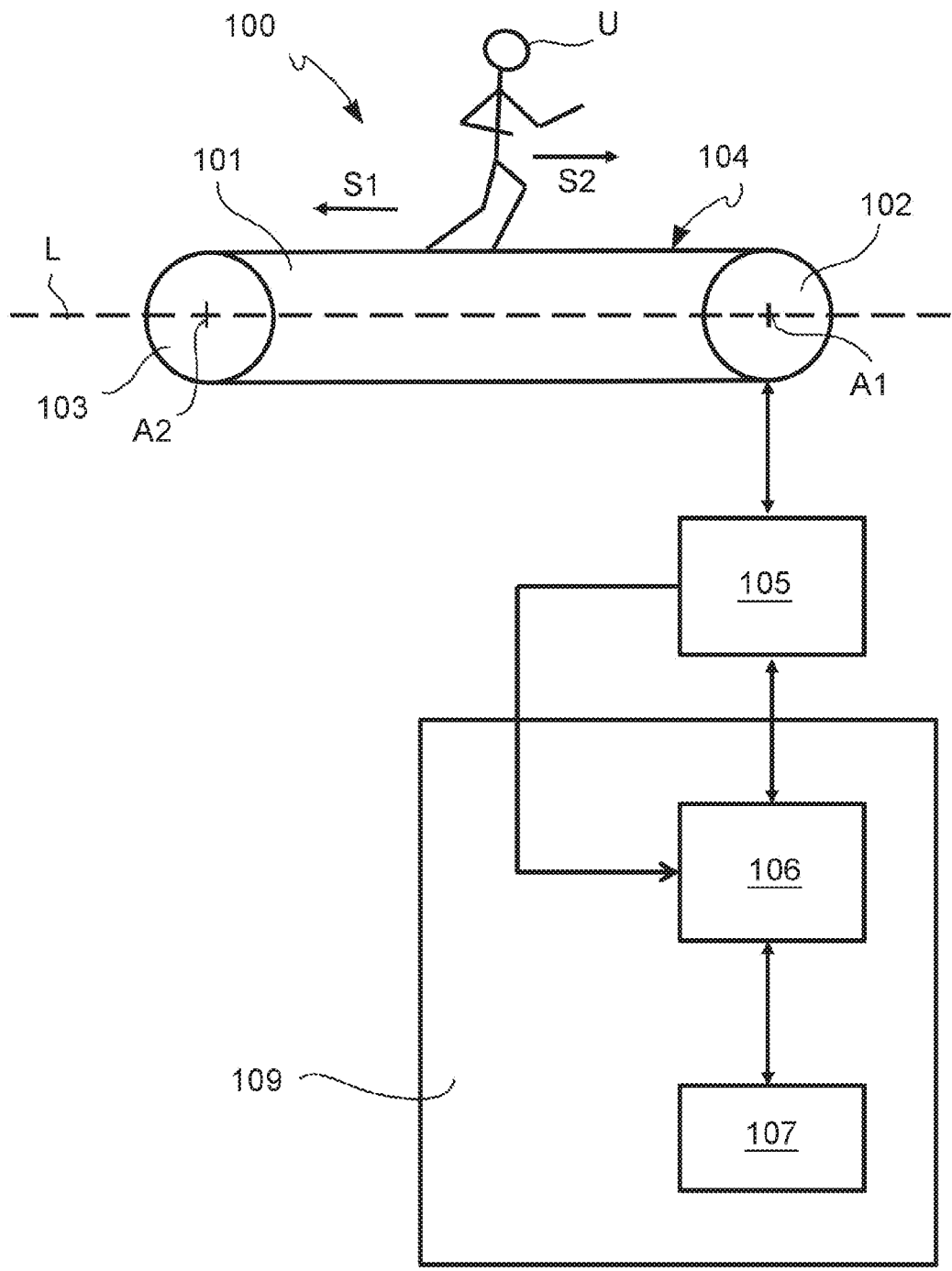
FIG. 1 shows, by means of a block scheme, a treadmill with adaptive control according to an embodiment of the present disclosure.

It is worth noting that equivalent or similar elements are indicated by the same numerical and/or alphanumerical reference in the aforesaid figures.

The reference numeral 100 indicates as a whole a treadmill with adaptive control, hereinafter also only treadmill or simply belt.

Figure 2:
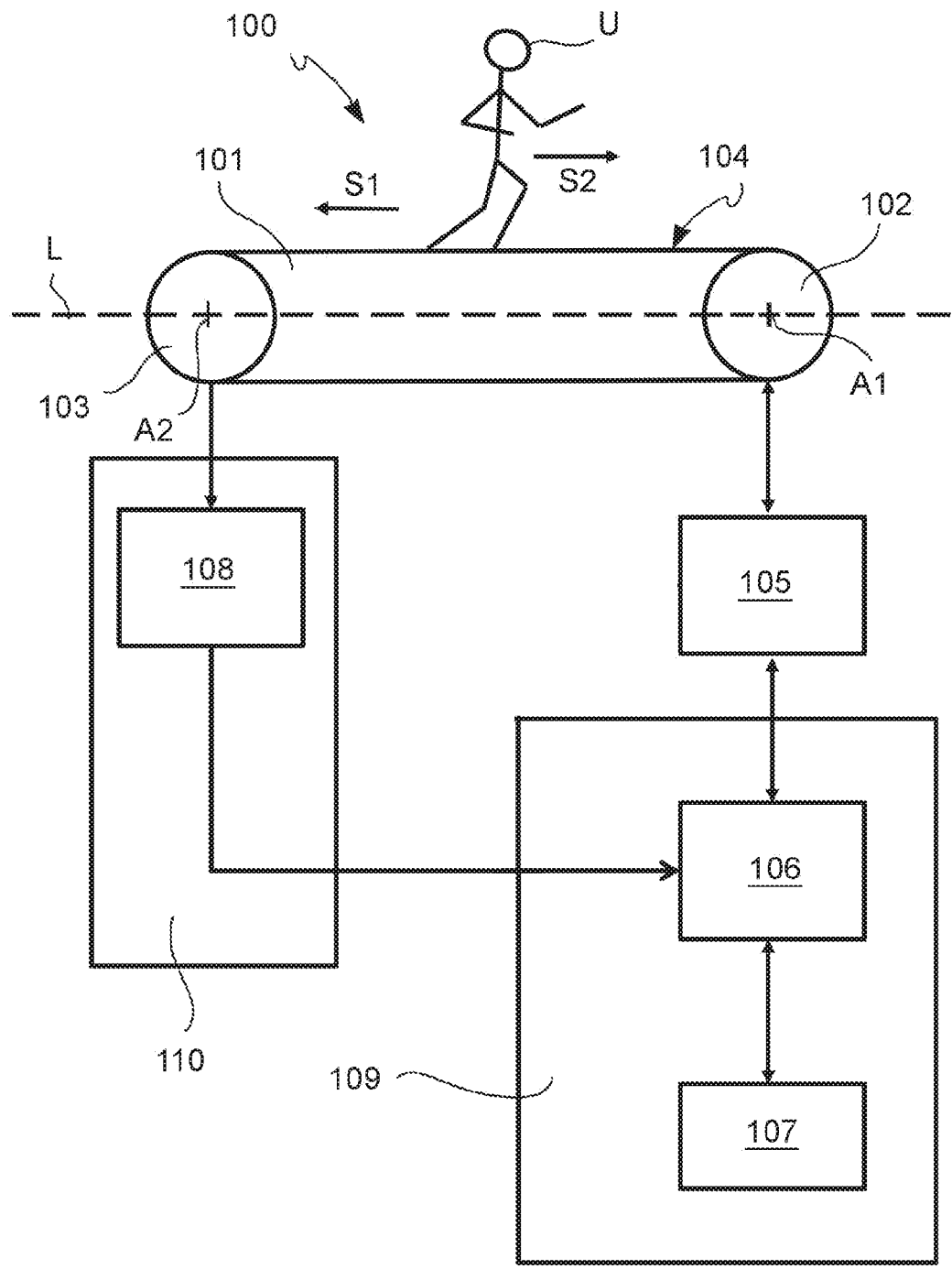
FIG. 2 shows, by means of a block scheme, a treadmill with adaptive control according to a further embodiment of the present disclosure.

It is worth noting that FIGS. 1 and 2 show some embodiments of the treadmill 100 and of some components simply by means of a block scheme in order to highlight the technical features which are essential and important for better understanding the present disclosure.

With particular reference to the embodiment shown in FIG. 1 and to the embodiment shown in FIG. 2, the treadmill 100 comprises a base 101 extending along a longitudinal axis L, indicated by a dashed line in the figure.

The base 101 comprises a first rotatable element 102 and a second rotatable element 103 adapted to rotate about respective rotation axes, a first rotation axis A1 for the first rotatable element 102 and a second rotation axis A2 for the second rotatable element 203, transversal to the longitudinal axis L of the base 101 of the treadmill 100.

It is worth noting that the first rotatable element 102 is arranged at a first end of the base 101, whilst the second rotatable element 103 is arranged at a second end of the base 101, opposite to said first end along the longitudinal axis L of the base 101.

The base 101 further comprises a physical exercise surface 104 operatively connected to the first rotatable element 102 and to the second rotatable element 103.

It is worth noting that the physical exercise surface 104, between the first rotatable element 102 and the second rotatable element 103, has a side profile which is substantially parallel with respect to the longitudinal axis L of the base 101.

For the purposes of the present description, "physical exercise surface" means the rotational surface of the treadmill on which a user U (diagrammatically shown in FIGS. 1 and 2), by placing his or her feet or lower limbs in general, can carry out a physical exercise, such as, for example, running, walking, thrusting exercises, or any other type of physical exercise that the treadmill 100 allows.

Furthermore, it is worth noting that "rotatable element" means any mechanical element adapted to rotate about a respective rotation axis so as to impart a rotation to the "physical exercise surface" operatively associated with one or more of these rotatable elements. The type of rotatable elements, some examples of which will be described below, depends on the type of physical exercise surface to be brought into rotation.

In greater detail, the rotation of the first rotatable element 102 drags in rotation also the physical exercise surface 104 and the second rotatable element 103. In entirely similar manner, the rotation of the second rotatable element 103 drags in rotation the first rotatable element 102 and the physical exercise surface 104.

In an embodiment (not shown in the figures), the physical exercise surface 104 comprises a belt wound about the first rotatable element 102 and the second rotatable element 103 and a support table, arranged between the first rotatable element 102 and the second rotatable element along the longitudinal axis L of the base 101, on which the belt defining the physical exercise surface 104 runs, adapted to support the physical exercise surface 104.

In this embodiment, the first rotatable element 102 and the second rotatable element 103 comprise two respective rollers, each rotationally coupled to the base 101 of the treadmill 100 at the two ends of the base 101, to which the belt is connected.

According to a further embodiment, the physical exercise surface 104 comprises a plurality of slats transversal to the longitudinal axis L of the base 101, conferring a slat conformation to the physical exercise surface 104.

In this embodiment, both the first rotatable element 102 and the second rotatable element 103 comprise two respective pulleys arranged near the side portions of the base 101, transversely to the longitudinal axis L of the base 101, adapted to support the plurality of slats at the side edges of each slat.

Furthermore, the physical exercise surface 104, at the side edges of the plurality of slats is supported by respective side guides fixed to the base, each side guide comprising a series of small rollers coupled in a freely rotatable manner to the base 101 on which the respective side edge of the plurality of slats runs.

In general, the treadmill 100 further comprises a frame (not shown in the figures) extending substantially in vertical direction with respect to the base 101.

The frame is a combination of uprights and tubular elements operatively connected to one another and distributed so as to define a supporting structure which at least in part surrounds the user U when he or she is on the physical exercise surface 104.

With reference again to the embodiment in FIG. 1 and to the embodiment in FIG. 2, the treadmill 100 further comprises a motor 105, e.g. an electrical motor of brushless or asynchronous type, operatively associated to at least one of said first rotatable element 102 and second rotatable element 103.

It is worth noting that in the description which follows and also in FIGS. 1 and 2, for the sake of convenience, the case in which the motor 105 is associated with the first rotatable element 102 is considered, taking into account that the motor 105 could be associated with the second rotatable element 103 in equivalent and alternative manner.

The motor 105, operatively associated with and controllable by a data processing unit (described below), is configured to set in rotation the first rotatable element 102 about the respective rotation axis, the first rotation axes A1. The rotation of the first rotatable element 102 drags in rotation the physical exercise surface 104, which also brings into rotation the second rotatable element 103.

When the physical exercise surface 104 is moving, the forward sense of the physical exercise surface 104, indicated by reference S1 in FIGS. 1 and 2, is opposite to the forward sense of the user U, indicated in FIGS. 1 and 2 by reference S2.

The treadmill 100 further comprises a data processing unit 106, e.g. a microprocessor or a microcontroller (inverter).

The treadmill 100 further comprises a memory unit 107, operatively connected to the data processing unit 106.

The memory unit 107 can be either internal or external (as shown in the FIGS. 1 and 2, for example) to the data processing unit 106.

It is worth noting that the memory unit 107 is configured to store one or more program codes which can be executed by the data processing unit 106 to control the treadmill 100, as will be described below.

The data processing unit 106 is configured to perform a method of adaptive control of the treadmill 100, which will be described hereinafter with respect to different embodiments.

With reference now to the embodiment in FIG. 1, the data processing unit 106 is advantageously configured to detect at least one first electrical parameter of the treadmill 100 representative of the interaction between the user U and the physical exercise surface 104. Such at least one first electrical parameter will be described below.

With this regard, the data processing unit 106 may comprise, in turn, a respective integrated detection unit for detecting said at least one first electrical parameter.

Furthermore, the data processing unit 106 may be configured to detect directly and automatically such at least one first electrical parameter and monitor the variations of electrical voltage/current of the motor or the variations of electrical voltage/current of the data processing unit 106 itself.

Indeed, the data processing unit 106, during the normal operation of the treadmill, generates electrical voltage and electrical current on the motor 105 for controlling it so that the data processing unit 106 can know its values directly.

In other words, the integrated detection unit may be the data processing unit 106 itself.

It is worth noting that the electrical voltage and the electrical current associated with the motor 105 and/or the data processing unit 106 are examples of said at least one first electrical parameter, as will be reasserted hereinafter.

According to a further embodiment (shown in FIG. 2), in combination with or alternatively to the embodiment in FIG. 1, the treadmill 100 comprises a detection unit 108 of at least one second parameter, distinct from said at least one first electrical parameter, representative of the interaction between the user U and the physical exercise surface 104.

Contrary to the embodiment shown in FIG. 1, the detection unit 108 is external to the data processing unit 106.

It is worth noting that the detection unit 108 may comprise one or more sensors for detecting said at least one second parameter representative of the interaction between the user U and the physical exercise surface 104, i.e. one or more sensors selected according to the parameter or to the combination of parameters which have to be detected to control the treadmill 100, according to one or more embodiments in combination with or alternatively to one another.

It is worth noting that in FIG. 2, by way of example, the detection unit 108 is diagrammatically shown as a single unit (single sensor).

The detection unit 108 is operatively associated with the data processing unit 106 to provide said at least one second parameter representative of the interaction between the user U and the physical exercise surface 104 detected by the detection unit 108 to the data processing unit 106.

With this regard, according to an embodiment, not shown in the figures, the data processing unit 106 and the detection unit 108 are respectively configured to receive and transmit said at least one second representative parameter detected by the detection unit 108.

In greater detail, the treadmill 100 comprises a first data communication module (not shown in FIG. 2) operatively associated with the data processing module 106 and a second data commutation module (also not shown in FIG. 2) operatively connected to the detection unit 108 configured to communicate with one another by means of a data communication channel of the wireless type (e.g. a data communication channel of Bluetooth, NFC or Wi-Fi type) or by means of a data connection channel of the wired type.

Turning back in general to the embodiment in FIG. 1 and to the embodiment in FIG. 2, it is worth noting that the data processing unit 106 and the memory unit 107 (and possibly also the respective data communication module, if present) may be distributed on a first electronic board 109 (e.g. a printed circuit).

In the second embodiment, the detection unit 108 (and possibly the respective data communication module) may be distributed on a second electronic board 110 (FIG. 2), e.g. a printed circuit.

According to an embodiment, shown in FIG. 2, the first electronic board 109 and the second electronic board 110 may be mutually distinct.

According to a further embodiment, alternative to the one just described and not shown in the figures, the first electronic board 109 and the second electronic board 110 may be the same electronic board, instead.

Hereinafter, with reference also to FIG. 3, a method 300 of adaptive control of the treadmill 100, hereinafter also method of adaptive control or simply method, will be described according to various embodiments.

Firstly, the Applicant remarks that the training of a user U on the physical exercise surface 104 is characterized by a sequence of steps of contact between the feet of the user U and the physical exercise surface 104.

According to the type of exercise that the user U can perform on the physical exercise surface 104, the sequence of steps of contact may comprise the alternation of a step of contact of the right foot and of a step of contact of the left foot, or the sequence of steps of subsequent contact of the same foot (right or left) or the alternation of sequences of steps of contact of a foot (right or left) and of the other (left or right).

The step of contact of a foot with the physical exercise surface 104 is representative of the contact of the sole of the foot, or at least a portion thereof, with the physical exercise surface 104.

In detail, the step of contact comprises a first initial step of impact, or simply step of impact, in which the foot strikes the physical exercise surface 104 and a second final step of release, or simply step of release, in which the foot detaches from the physical exercise surface 104.

The action of the foot of the user U, when the training speed is increased or decreased, generates a speed variation of the physical exercise surface 104 with respect to the initial speed (or to the instant before such action) during the step of contact (thus of impact and release) and, either alternatively or in combination, generates a variation of the cadence, i.e. of the frequency of footsteps in a set period of time (e.g. per minute), correlated with the frequency of the steps of contact (thus of impact and release).

More in detail, when the user increases the training speed, the user's foot, in the instant of time immediately before the impact, has a higher relative speed than the physical exercise surface 104 and generates on it a thrust during the step of contact (thus of impact and release) in the forward sense S1 of the physical exercise surface 104 and, either alternatively or in combination, increases the cadence, and thus the frequency, of the steps of contact (thus of impact and release).

Conversely, when the user decreases the training speed, in the instant of time immediately preceding the impact, the relative speed of the user's foot is lower than the physical exercise surface 104 and generates a deceleration on it during the step of contact (thus of impact and/or release) in the forward sense S1 of the physical exercise surface 104 and, either alternatively or in combination, decreases the cadence, and thus the frequency, of the steps of contact (thus of impact and release).

The consequence of such actions by the user U, i.e. of increasing or decreasing the training speed, described above, is the variation of said at least one first electrical parameter of the treadmill 100 representative of the interaction between the user U and the physical exercise surface 104 and possibly, in the embodiment of FIG. 2, also of said at least one second parameter representative of the interaction between the user U and the physical exercise surface 104.

Of course, the interaction between user U and the physical exercise surface 104 may occur during the step of contact (i.e. in the respective steps of impact and release), so that a value of the representative parameter is associated with each step of contact (i.e. of impact and release).

Consequently, a sequence of values of said at least one first electrical parameter and, if present, of said at least one second parameter corresponds to the sequence of steps of contact (thus of impact and release), as mentioned above, characteristic of the training of the user on the exercise surface 104.

For the purposes of the present disclosure, "at least one first electrical parameter representative of the interaction between the user and the physical exercise surface", or simply "at least one first electrical parameter representative of the interaction", or "at least one first representative electrical parameter", means an electrical parameter which can be detected on the treadmill directly by the data processing unit 106 (possibly with the help of the respective detection unit integrated therein), the variation of which is correlated with the action of the user U on the physical exercise surface 104 during the use of the treadmill 100, i.e. the variation is correlated with the training speed increasing or decreasing action by the user U (running, walking, thrusting exercises) on the physical exercise surface 104.

Example of such at least one first electrical parameter is an electrical quantity, such as, for example, the electrical voltage or the electrical current associated with the motor 105 and/or with the data processing unit 106.

With this regard, if the detection unit of said at least one electrical parameter integrated inside the data processing unit 106 is envisaged, such data processing unit 106 may comprise a detection sensor of at least one electrical quantity (electrical current sensor, electrical voltage sensor or other technical equivalent).

Furthermore, as mentioned above, the data processing unit 106 may be configured to detect directly and automatically such at least one first electrical parameter and to monitor the electrical voltage/current variations of the motor or the electrical voltage/current variations of the data processing unit 106 itself.

Indeed, the data processing unit 106, during the normal operation of the treadmill, generates electrical voltage and electrical current on the motor 105 for controlling it, so that the data processing unit 106 can know its values directly.

In other words, the integrated detection unit may be the data processing unit 106 itself.

For the purposes of the present disclosure, "at least one second parameter representative of the interaction between the user and the physical exercise surface", or simply "at least one second parameter representative of the interaction", or "at least one second representative parameter" means a further parameter which can be detected on the treadmill by the detection unit 108 (embodiment in FIG. 2), the variation of which is correlated with the action of the user U on the physical exercise surface 104 during the use of the treadmill 100, i.e. the variation is correlated with the training speed increasing or decreasing action by the user U (running, walking, pushing exercises) on the physical exercise surface 104.

Examples of such at least one second parameter are:

the forward speed of the physical exercise surface 104 or the rotation speed of the first rotatable element 102 or of the second rotatable element 103 or of the motor 105;

the mechanical deformation due to the load of the user U on the first rotatable element 102 or on the second rotatable element 103, or on the transmission belt coupling to the rotation shaft of the motor 105.

With this regard, the detection unit 108 may comprise, either alternatively to or in combination with one another, a speed sensor (with direct or indirect measurement, e.g.: encoder, accelerometer, gyroscope, a combination of the above or other technical equivalent), a deformation sensor (strain meter, load cell, pressure sensor, torque meter, a combination of the above or other technical equivalent).

Figure 3:
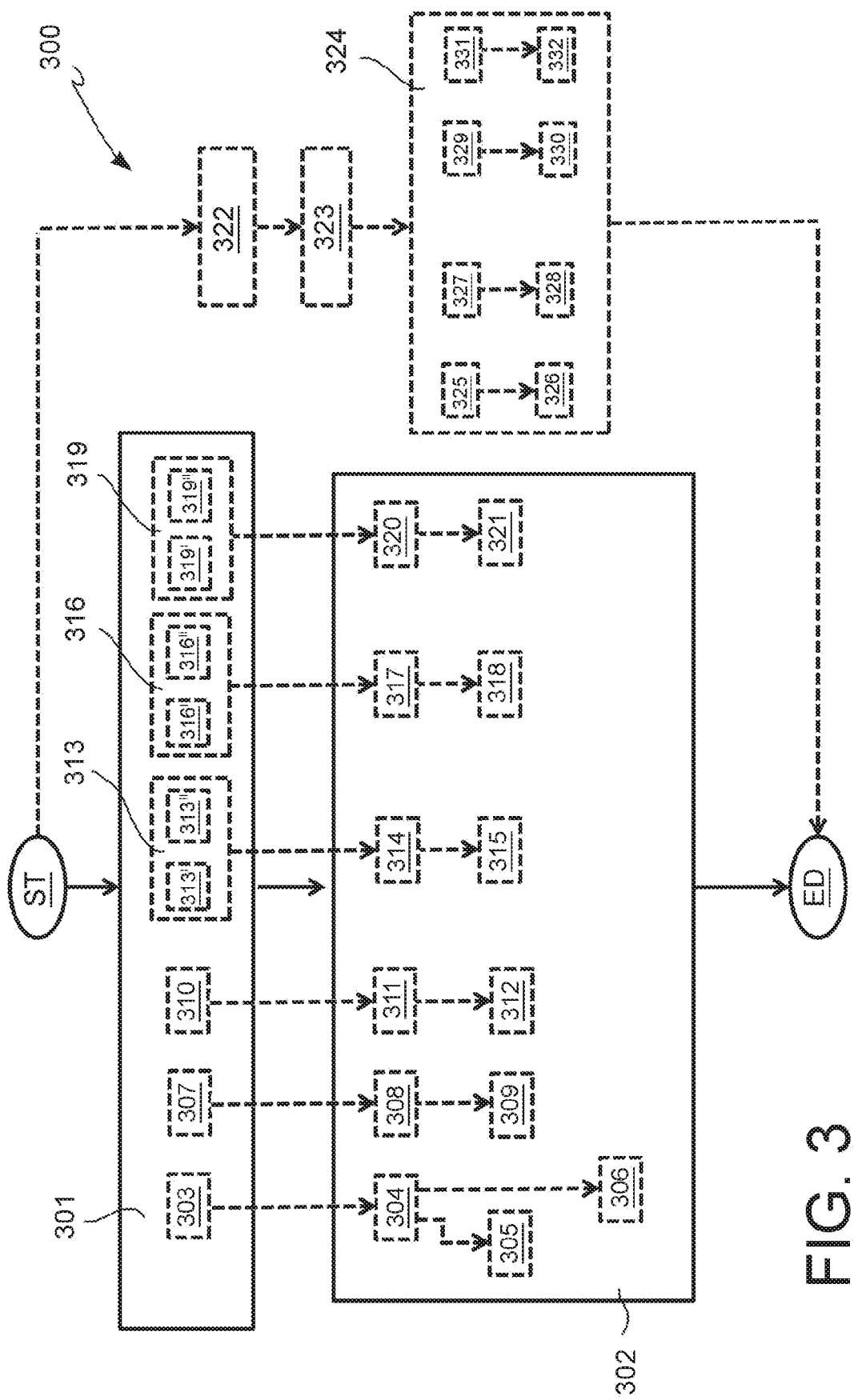
FIG. 3 shows, by means of a block chart, a method of adaptive control of a treadmill according to an embodiment of the present disclosure.

With reference now also to the diagram in FIG. 3, the method 300 comprises a symbolic step of starting ST.

The method 300 comprises a step of determining 301, by a data processing unit 106 of the treadmill 100, at least a first electrical parameter of the treadmill 100 representative of the interaction between a user U and the physical exercise surface 104 of the treadmill 100.

The method further comprises a step of controlling 302, by the data processing unit 106 of the treadmill 100, the motor 105 of the treadmill 100 on the basis of said at least one first parameter of the treadmill 100 representative of the interaction between the user U and the physical exercise surface 104 determined by the data processing unit 106.

In an embodiment, the step of controlling 302 is performed by the data processing unit 106, on the basis of the variation of said at least one first electrical parameter generated by the training speed increasing or decreasing action by a user U during a sequence of steps of contact (thus of impact and release) between the feet of the user U and the physical exercise surface 104.

It is worth noting that the sequence of steps of contact could comprise the sequence of steps of alternating contact of the right foot and of the left foot or the sequence of steps of contact of the same foot (right or left).

It is worth noting that "sequence of steps of contact (and thus of impact and release)" means the last step of contact (thus of impact and release) and at least one of the previous steps of contact (thus of impact and release).

In greater detail, as shown in FIG. 3, the step of determining 301 comprises a step of detecting 303, by the data processing unit 106, a sequence of values of said at least one first electrical parameter, corresponding to a sequence of steps of contact (thus of impact and release) of the user's feet with the physical exercise surface 104.

The at least one first electrical parameter, as defined above, is an electrical quantity, such as for example the electrical current absorbed by the motor 105, the regenerative electrical voltage of the data processing unit 106 or both.

The step of controlling 302 comprises a step of comparing 304, by the data processing unit 106, the detected value of said at least one first electrical parameter corresponding to the last step of contact (thus of impact and release) with the detected value of said at least one parameter corresponding to at least one of the previous steps of contact (thus of impact and release).

Finally, the step of controlling 302 comprises a step of controlling 305 the motor 105, by the data processing unit 106, on the basis of said comparison.

Of course, if the user U does not apply any training speed increasing or decreasing action, and i.e. substantially maintains a constant training speed (the variation of which is not significant enough to be detected, i.e. is lower than 0.1 km/h of increase or decrease), the step of controlling 302 comprises a step of controlling 306 the motor 105, by the data processing unit 106, to maintain the forward speed of the physical exercise surface, and thus the training speed of the user U, constant.

As described above, the training speed increasing action by the user generates a thrust on the physical exercise surface 104 in the forward sense S1 of the physical exercise surface 104 and/or an increase of the cadence during the sequence of steps of contact (thus of impact and release).

The thrust on the physical exercise surface 104 generates an excess of energy on the motor 105, which, by generative effect, is given back to the data processing unit 106, generating an electrical voltage variation on at least one electrical/electronic component of the data processing unit 106, which can be detected by the data processing unit 106 itself.

In an embodiment, also shown in FIG. 3, the step of controlling 302 is performed, by the data processing unit 106, on the basis of the variation of the electrical voltage in the data processing unit 106 itself generated by the training speed increasing or decreasing action by a user during a sequence of steps of contact (thus of impact and release) of the feet of the user U on the physical exercise surface 104.

In greater detail, the step of determining 301 comprises a step of detecting 307, by the data processing unit 106, a sequence of electrical voltage values, associated with the sequence of steps of contact (thus of impact and release) of the feet of the user U on the physical exercise surface 104.

Furthermore, the step of controlling 302 comprises a step of comparing 308, by the data processing unit 106, the detected value of the electrical voltage corresponding to the last step of contact (thus of impact and release) with the value of the electrical voltage corresponding to at least one of the previous steps of contact (thus of impact and release).

If the detected electrical voltage value corresponding to the last step of contact (thus of impact and release) is higher than the electrical voltage value corresponding to at least one of the previous steps of contact (thus of impact and release), the step of controlling 302 comprises a step of controlling 309 the motor 105, by the data processing unit (106), so as to increase the forward speed of the physical exercise surface 104 by a value proportional to the magnitude of the measured difference.

In a further embodiment, the step of determining 301 comprises a step of detecting 310, by the data processing unit 106, a sequence of maximum electrical voltage values associated with the sequence of steps of release of the user's feet with the physical exercise surface 104.

Furthermore, the step of controlling 302 comprises a step of comparing 311, by the data processing unit 106, the last maximum electrical voltage value associated with the last step of release with at least one maximum electrical voltage value corresponding to at least one of the previous steps of release.

If the last detected maximum electrical voltage value is higher than at least one maximum electrical voltage value corresponding to at least one of the previous steps of release, the step of controlling 302 comprises a step of controlling 312 the motor 105, by the data processing unit 106, to increase the forward speed of the physical exercise surface 104 by a value proportional to the magnitude of the difference measured.

Indeed, the step of releasing the effect of the thrust of the user on the physical exercise surface 104 in direction S1 is maximum.

In other words, the method 300 allows detecting the variation of the electrical voltage, in particular the generation or the increase of the electrical voltage associated with the data processing unit 106 or to at least one electrical/electronic component thereof.

In this embodiment, the step of controlling 302 the motor 105 is advantageously performed, by the data processing unit 106, by increasing the forward speed of the physical exercise surface 104 to adapt automatically to the action of the user U of accelerating, without the latter imparting the speed increasing control.

In a further embodiment, either alternatively to or in combination with those described above, the step of controlling 302 the motor 105 is performed, by the data processing unit 106, on the basis of the variation of the electrical current absorbed by the motor 105 during a sequence of steps of contact (thus of impact and release) of the feet on the physical exercise surface 104, generated by the increase of the cadence when the user U increases the training speed.

In particular, the step of controlling 302 the motor 105 is performed, by the data processing unit 106, on the basis of the variation of the frequency of the electrical current absorption peaks of the motor 105 during a sequence of steps of contact (thus of impact and release) of the feet on the physical exercise surface 104, generated by the increase of the cadence when the user U increases the training speed.

More in detail, the electrical current absorbed by the motor 105, provided by the data processing unit 106, has a periodical trend with peaks (maximum values) associated with each step of contact of the feet, in particular with the step of impact and, when the user U increases the cadence, the frequency of the electrical current absorption peaks also increases as a consequence.

In other words, the time distance between one impact and the previous one(s) is reduced and such variation can be found in the trend of the absorbed electrical current.

In this embodiment, the step of determining 301 comprises a further step of determining 313, by the data processing unit 106, the frequency of the electrical current absorption peaks of the motor 105 during a sequence of steps of contact (thus of impact and release) of the feet on the physical exercise surface 104.

The step of controlling 302 further comprises a step of comparing 314, by the data processing unit 106, the last determined electrical current absorption peak and at least two determined electrical current absorption peaks before them to determine the increase in the frequency of the electrical current absorption peaks of the motor 105, during a sequence of steps of contact (thus of impact and release) of the feet on the physical exercise surface 104 when the user U increases the training speed.

The step of controlling 302 further comprises a step of controlling 315 the motor 105, by the data processing unit 106, in order to increase the forward speed of the physical exercise surface 104 on the basis of the increase in the frequency of the electrical current absorption peaks of the motor 105.

In this embodiment, the method 300 allows controlling the motor 105 by increasing the forward speed of the physical exercise surface 104 to adapt automatically to the user's action of accelerating without the latter imparting the speed increasing control.

The forward speed of the physical exercise surface 104 is increased on the basis of the increase in the frequency of the electrical current absorption peaks.

In an embodiment, the further step of determining 313 comprises a step of detecting 313', by the data processing unit 106, the variation of the electrical current absorbed by the motor 105, in particular the variation (increase) of the frequency of the electrical current absorption peaks of the motor 105.

In a further embodiment, alternative to the one above, the further step of determining 313 comprises a step of calculating 313", by the data processing unit 106, the variation of the electrical current absorbed by the motor 105, in particular the variation (increase) of the frequency of the electrical current absorption peaks of the motor 105.

According to different embodiments, the two forms of control above, respectively by means of electrical voltage and by means of the electrical current, may be alternative or in mutual combination.

As described above, the user's action of decreasing the training speed generates a deceleration of the physical exercise surface 104 in the forward sense S1 of the physical exercise surface 104 and/or a decrease of the cadence during the sequence of the step of contact (thus of impact and release) of the feet on the physical exercise surface 104.

In an embodiment, the step of controlling 302 the motor 105 is performed, by the data processing unit 106, on the basis of the variation of the electrical current absorbed by the motor during the sequence of steps of contact (thus of impact and release) of the foot, generated by the increase of the electrical current absorption peaks when the user U decreases the training speed.

In particular, the step of controlling 302 the motor 105 is performed, by the data processing unit 106, on the basis of the variation of the electrical current absorption peaks of the motor 105 during a sequence of steps of contact of the feet on the physical exercise surface 104, generated by the action of the user U to decrease the training speed.

More in detail, the electrical current absorbed by the motor 105, supplied by the data processing unit 106, has a periodical trend with peaks (maximum values) associated with each step of contact of the feet, in particular with the step of impact, on the physical exercise surface 104 and, when the user decreases the training speed, the electrical current absorption peaks of the motor 105 increase by effect of the action of the user U on the physical exercise surface 104.

In this embodiment, the step of determining 301 comprises a further step of determining 316, by the data processing unit 106, a sequence of the electrical current absorption peaks of the motor 105 associated with the sequence of steps of contact, in particular the steps of impact, of the user's feet on the physical exercise surface 104.

The step of controlling 302 further comprises a step of comparing 317, by the data processing unit 106, the determined electrical current peak value corresponding to the last step of contact (impact) with the determined electrical current peak value corresponding to at least one of the previous steps of contact (impact).

If the determined current peak value corresponding to the last step of contact (impact) is higher than the determined current peak value corresponding to at least one of the previous steps of contact (impact), the step of controlling 302 comprises a step of controlling 318 the motor 105, by the data processing unit 106, to decrease the forward speed of the physical exercise surface 104 by a value proportional to the magnitude of the measured difference.

More in detail, the data processing unit 106 is configured to detect the increase of the value of the electrical current absorption peaks of the motor 105, during a sequence of steps of impact of the foot when the user decreases the training speed.

In other words, in this embodiment, the method 300 allows determining the variation of the electrical current absorbed by the motor 105, in particular the increase of the value of the electrical current absorption peaks of the motor 105.

Furthermore, the method 300 advantageously allows controlling the motor 105 by decreasing the forward speed of the physical exercise surface 104 to adapt automatically to the action of the user U of decelerating, without the latter imparting the control of decreasing the speed.

In an embodiment, the further step of determining 316 comprises a step of detecting 316', by the data processing unit 106, the increase of the value of the electrical current absorption peaks of the motor 105, related to at least one of the previous current peaks.

In a further embodiment, alternative to the one above, the further step of determining 316 comprises a step of calculating 316", by the data processing unit 106, the increase of the value of the electrical current absorption peaks of the motor 105, related to at least one of the previous current peaks.

In a further embodiment, the step of controlling 302 the motor 105 is performed, by the data processing unit 106, on the basis of the variation of the electrical current absorbed by the motor during a sequence of steps of contact (thus of impact and release) of the foot on the physical exercises surface 104, generated by the decrease of the cadence when the user U decreases the training speed.

In particular, the step of controlling 302 the motor 105 is performed, by the data processing unit 106, on the basis of the variation of the frequency of the electrical current absorption peaks of the motor 105 during a sequence of steps of contact (thus of impact and release of the foot), generated by the decrease of the cadence when the user U decreases the training speed.

More in detail, the electrical current absorbed by the motor 105, provided by the data processing unit 106, has a periodical trend with peaks (maximum values) associated with each step of contact of the feet, in particular during the step of impact and, when the user decreases the cadence, the frequency of the electrical current absorption peaks of the motor 105 decreases as a consequence too.

In other words, the time distance between one impact and the previous one(s) increases, and such variation can be found in the trend of the electrical current absorbed by the motor 105.

In this embodiment, the step of determining 301 comprises a further step of determining 319, by the data processing unit 106, the frequency of the electrical current absorption peaks of the motor 105 during a sequence of steps of contact (thus of impact and release) of the foot on the physical exercise surface 104 when the user U decreases the training speed.

The step of controlling 302 further comprises a step of comparing 320, by the data processing unit 106, the last determined electrical current absorption peak and at least two determined electrical current peaks before it to determine the decrease in the frequency of the electrical current absorption peaks of the motor 105, during a sequence of steps of contact (thus of impact and release) of the feet on the physical exercise surface 104 when the user U decreases the cadence, and thus the training speed.

The step of controlling 302 further comprises a step of controlling 321 the motor 105, by the data processing unit 106, in order to decrease the forward speed of the physical exercise surface 104 on the basis of the decrease of the frequency of the determined electrical current absorption peaks of the motor 105.

In an embodiment, the further step of determining 319 comprises a step of detecting 319', by the data processing unit 106, a decrease of the frequency of the electrical current absorption peaks of the motor 105, related to the last electrical current absorption peak detected and at least two electrical current peaks before them.

In a further embodiment, the further step of determining 319 comprises a step of calculating 319", by the data processing unit 106, a decrease of the frequency of electrical current absorption peaks of the motor 105, related to the last electrical current absorption peak and at least two electrical current peaks before them.

According to a further embodiment, either alternative to or in combination with those described above, the method 300 further comprises a step of detecting 322, by the detection unit 108 (FIG. 2), at least one second parameter, distinct from said at least one first electrical parameter, representative of the interaction between the user U and the physical exercise surface 104.

The second parameter was defined above.

Furthermore, in this embodiment, the method 300 comprises a step of sending 323 said at least one second parameter to the data processing unit 106, by the detection unit 108.

The method 300 further comprises a step of controlling 324 the motor 105, by the data processing unit 106, on the basis of said at least one second parameter detected by the detection unit 108.

It is worth noting that the control of the motor 105, by the data processing unit 106, on the basis of said at least one second parameter is integrative with respect to the control of the motor 105, also by the first data processing unit 106, on the basis of said at least one first electrical parameter, as it is performed after the detection, by means of external sensors (detection unit 108), of other parameters on the basis of which to control the treadmill 100, such as, for example, the forward speed of the physical exercise surface and the mechanical deformation thereof, parameters that the data processing unit 106, predisposed for determining only the at least one first electrical parameter (electrical quantity), cannot detect automatically.

In greater detail, in an embodiment, the step of controlling 324 the motor 105 is performed, by the data processing unit 106, by varying the speed of the motor 105, i.e. by varying the electrical power voltage and/or its frequency, on the basis of one or more program codes stored in the storing unit 107 and/or on the basis of said at least one second parameter representative of the interaction between the user U and the physical exercise surface 104 detected by the detection unit 108.

In an embodiment, the step of controlling 324 the motor 105 is performed by the data processing unit 106, on the basis of the variation of said at least one second electrical parameter generated by the training speed increasing and/or decreasing action by the user U during a sequence of steps of contact (thus of impact and release) of the foot (as described above).

With this regard, the step of determining 322 is performed, by the detection unit 108, to detect a sequence of values of said at least one second representative parameter, corresponding to a sequence of steps of contact (thus of impact and release) of the feet of the user U on the physical exercise surface 104.

Successively, the step of controlling 324 comprises a step of comparing 325, by the data processing unit 106, the value of said at least one second representative parameter corresponding to the last step of contact (thus of impact and release) with the value of said at least a second representative parameter corresponding to at least one of the previous steps of contact (thus of impact and release).

Furthermore, the step of controlling 324 comprises a step of controlling 326 the motor 105, by the data processing unit 106, on the basis of said comparison, proportionally to the magnitude of the detected deviation.

According to a further embodiment, said at least one second parameter representative of the interaction between the user U and the physical exercise surface 104 which can be detected by the detection unit 108 is an electrical disturbance of the motor 105, as for example the absorbed electrical current or the electrical voltage.

In such case, the detection unit 108 comprises a detection sensor of such electrical quantity (or disturbance) of the motor 105 (for example, an electrical current sensor or an electrical voltage sensor).

In this embodiment, the step of controlling 324 comprises a step of comparing 327, by the data processing unit 106, the electrical disturbance value detected with a reference value (which may be the value of the previously detected second representative parameter) to determine a deviation correlated with the actual action of the user U on the physical exercise surface U.

The step of controlling 324 further comprises a step of controlling 328 the motor 105, by the data processing unit 106, in order to vary the forward speed of the physical exercise surface 104 of the treadmill 100 on the basis of the determined deviation of the electrical disturbance.

In this case, the motor 105 is controlled by the data processing unit 106, by modulating at least one electrical control quantity of the motor 105 (i.e. either the electrical current or the electrical power voltage of the motor 105) on the basis of the deviation determined by the electrical disturbance.

In a further embodiment, either alternative to or in combination with the one above, said at least one second parameter representative of the action of the user U on the physical exercise surface 104 which can be detected by the detection unit 108 may be the forward speed of the physical exercise surface 104 (of the first rotatable element 102 or of the second rotatable element 103 or of the motor 105).

In this case, the detection unit 108 comprises, for example a speed sensor (accelerometric, gyroscope, a combination of the above or other technical equivalent).

In this embodiment, the step of controlling 324 includes a step of comparing 329, by the data processing unit 106, the detected forward speed value of the physical exercise surface 104 with a reference value (which may be the value of the previously detected second representative parameter) to determine a deviation correlated with the actual action of the user U on the physical exercise surface 104.

The step of controlling 342 thus comprises a step of controlling 330 the motor 105, by the data processing unit 106, in order to correspondingly vary the forward speed of the physical exercise surface 104 of the treadmill 100 on the basis of the determined deviation of the forward speed of the physical exercise surface 104.

In a further embodiment, said at least one second parameter representative of the action of the user U on the physical exercise surface 104 detected by the detection unit 108 may be the mechanical deformation due to the load of the user U on either said first rotatable element 102 or second rotatable element 103.

In this embodiment, the detection unit 108 thus comprises a deformation sensor (strain meter, load cell, pressure sensor, a combination of the above or other technical equivalent).

In this embodiment, the step of controlling 324 includes a step of comparing 331, by the data processing unit 106, the value of the mechanical deformation value detected with a reference value (which may be the value of the previously detected second representative parameter) to determine a deviation correlated with the actual action of the user U on the physical exercise surface 104.

The step of controlling 324 further comprises a step of controlling 332 the motor 105, by the data processing unit 106, in order to vary the forward speed of the physical exercise surface 104 of the treadmill 100 on the basis of the determined deviation.

The method 200 comprises a symbolic step of ending ED.

According to a further aspect of the present disclosure, a program product can be loaded in a memory unit (e.g. the memory unit 107 of the treadmill 100) of a computer (e.g. the data processing unit 106 of the treadmill 100).

The program product can be executed by the data processing unit 106 of the electronic computer (treadmill 100) to execute the steps of the method 300 of adaptive control of the treadmill 100, described above with reference to FIG. 3 and according to its various embodiments.

As can be seen, the purpose of the disclosure is achieved because the treadmill with adaptive control 100 has the following advantages.

Indeed, by virtue of the treadmill 100 of the disclosure, the user U can (either voluntarily or involuntarily) with his or her action (interaction) with the physical exercise surface 104 (belt or slat) control the forward speed of the physical exercise surface 104 making his or her physical activity (running, walking or pushing exercises) as natural as possible, without excessive efforts or traumas, still remaining within safety conditions.

More in detail, by virtue of the treadmill 100 of the disclosure, the user U with his or her action on the physical exercise surface 104 (belt or slat) may generate a decrease in the forward speed of the physical exercise surface 104, if for example the user cannot keep up with the forward speed of the physical exercise surface 104, or, can generate an increase of the forward speed of the physical exercise surface 104, if the user can run faster than the forward speed of the physical exercise surface or if the user can apply a thrust on the physical exercise surface 104.

In the treadmill 100 of the disclosure, it is possible to determine (detect/calculate) the disturbances that the user U may create during the action/interaction on the physical exercise surface 104 (belt or slat), by comparing the value of at least one respective parameter detected with the reference value (previously detected value) controlling in feedback the motor 105 itself, thus the forward speed on the physical exercise surface 104, on the basis of the entity of the deviation (variation) of the detected parameter value with the reference value (previous value).

As mentioned above, such parameter may be an electrical quantity (electrical voltage, electrical current draw) that the data processing unit 106 may determine directly and automatically to control the motor 105 (thus the forward speed of the physical exercise surface 104 or also of the motor 105 or of the first rotatable element 102 and the second rotatable element 103) and/or of the load of the user U on the first rotatable element 102 and/or second rotatable element 103.

So, the advantage of being able to allow the user U to perform the physical activity (running, walking or thrusting exercises) as naturally as possible is apparent.

Furthermore, in an embodiment, the presence of the detection unit 108 external to the data processing unit 106 allows integrating the at least one first electrical parameter which can be detected directly and automatically by the data processing unit 106 with at least one second parameter, which cannot be detected by the data processing unit, which can be detected by the detection unit 108 and to control the motor 105 (thus the forward speed of the physical exercise surface 104) of the treadmill 100 more accurately.

This is not allowed on the common treadmills of the prior art, in which the forward speed of the belt or slat is set at the beginning to a value which is maintained constant for the entire duration of the physical activity, not allowing the user to run/walk in natural manner.

A person skilled in the art will be able to make changes, adaptations and replacements of elements with functionally equivalent ones to the embodiments of the treadmill with adaptive control, of the method of adaptive control of such treadmill and of the related program product described above, without departing from the scope of protection of the following claims. All the features described above as belonging to one possible embodiment may be implemented independently from the other described embodiments.

The invention claimed is:

1. A method of adaptive control of a treadmill, the treadmill comprising a base extending along a longitudinal axis, said base comprising:
    a first rotatable element and a second rotatable element adapted to rotate around respective rotation axes transverse to the longitudinal axis of the base;
    a physical exercise surface operatively connected to the first rotatable element and to the second rotatable element;
    a motor operatively associated with at least one of said first rotatable element and said second rotatable element, the motor being configured for setting in rotation the first rotatable element and the second rotatable element, and dragging in rotation the physical exercise surface;
    the method comprising steps of:
        determining, by a data processing unit of the treadmill, at least a first electrical parameter of the treadmill representative of interaction between a user and the physical exercise surface of the treadmill; variation of said at least a first electrical parameter of the treadmill representative of the interaction between the user and the physical exercise surface of the treadmill is correlated with action of the user on the physical exercise surface during use of the treadmill increasing or decreasing training speed of the physical exercise surface;
        controlling, by the data processing unit of the treadmill, the motor of the treadmill based on said at least a first electrical parameter of the treadmill representative of the interaction between the user and the physical exercise surface detected by the data processing unit;
        increasing the training speed of the physical exercise surface by the motor of the treadmill based on the variation of said at least a first electrical parameter of the treadmill representative of the interaction between the user and the physical exercise surface of the treadmill correlated with the action of the user on the physical exercise surface increasing by the user the training speed of the physical exercise surface;
        decreasing the training speed of the physical exercise surface by the motor of the treadmill based on the variation of said at least a first electrical parameter of the treadmill representative of the interaction between the user and the physical exercise surface of the treadmill correlated with the action of the user on the physical exercise surface decreasing by the user the training speed of the physical exercise surface.

2. The method according to claim 1, wherein the step of determining comprises a step of detecting, by the data processing unit, a sequence of values of said at least one first electrical parameter corresponding to a sequence of steps of contact of a user's feet with the physical exercise surface.

3. The method according to claim 2, wherein the step of controlling comprises steps of:
    comparing, by the data processing unit, the detected value of said at least one first electrical parameter corresponding to a last step of contact with the value detected of said at least one parameter corresponding to at least one of the previous steps of contact;
    controlling the motor, by the data processing unit based on said comparison.

4. The method according to claim 1, wherein the step of determining comprises a step of detecting, by the data processing unit, a sequence of electrical voltage values associated with a sequence of steps of contact of the user's feet on the physical exercise surface.

5. The method according to claim 4, wherein the step of controlling comprises steps of:
    comparing, by the data processing unit, the detected electrical voltage value corresponding to the last step of contact with the electrical voltage value corresponding to at least one of the previous steps of contact;
    if the detected electrical voltage value corresponding to the last step of contact exceeds the electrical voltage value corresponding to at least one of the previous steps of contact, controlling the motor, by the data processing unit, to increase forward speed of the physical exercise surface by a value proportional to a magnitude of the difference measured.

6. The method according to claim 1, wherein the step of determining comprises a step of detecting, by the data processing unit, a sequence of maximum electrical voltage values associated with a sequence of steps of release of the user's feet with the physical exercise surface.

7. The method according to claim 6, wherein the step of controlling comprises steps of:
    comparing, by the data processing unit a last maximum electrical voltage value associated with the last step of release with a maximum electrical voltage value corresponding to at least one of the previous steps of release;
    if the last detected maximum electrical voltage value is higher than at least one maximum electrical voltage value corresponding to at least one of the previous steps of release, controlling the motor, by the data processing unit, to increase the forward speed of the physical exercise surface by a value proportional to the magnitude of the difference measured.

8. A treadmill comprising:
    a base extending along a longitudinal axis, said base comprising:
    a first rotatable element and a second rotatable element adapted to rotate around respective rotation axes transverse to the longitudinal axis of the base;
    a physical exercise surface operatively connected to the first rotatable element and to the second rotatable element;
    a motor operatively associated to at least one of said first rotatable element and said second rotatable element, the motor being configured for setting in rotation said at least one of said first rotatable element and second rotatable element and dragging in rotation the physical exercise surface;
    a data processing unit, the motor being operatively associated with the data processing unit, the data processing unit being configured to:

determine at least a first electrical parameter of the treadmill representative of interaction between a user and the physical exercise surface of the treadmill; variation of said at least a first electrical parameter of the treadmill representative of the interaction between the user and the physical exercise surface of the treadmill is correlated with action of the user on the physical exercise surface during use of the treadmill increasing or decreasing training speed of the physical exercise surface;

control the motor based on said at least a first electrical parameter of the treadmill representative of the interaction between the user and the physical exercise surface detected by the data processing unit;

increase the training speed of the physical exercise surface by the motor of the treadmill based on the variation of said at least a first electrical parameter of the treadmill representative of the interaction between the user and the physical exercise surface of the treadmill correlated with the action of the user on the physical exercise surface increasing the training speed of the physical exercise surface;

decrease the training speed of the physical exercise surface by the motor of the treadmill based on the variation of said at least a first electrical parameter of the treadmill representative of the interaction between the user and the physical exercise surface of the treadmill correlated with the action of the user on the physical exercise surface decreasing the training speed on the physical exercise surface.

9. A program product configured to be loaded to a memory unit of an electronic computer, the program product being executed by the data processing unit of the electronic computer to execute the steps of:

determining, by a data processing unit of the treadmill, at least a first electrical parameter of the treadmill representative of interaction between a user and the physical exercise surface of the treadmill; variation of said at least a first electrical parameter of the treadmill representative of the interaction between the user and the physical exercise surface of the treadmill is correlated with action of the user on the physical exercise surface during use of the treadmill increasing or decreasing training speed of the physical exercise surface;

controlling, by the data processing unit of the treadmill, the motor of the treadmill based on said at least a first electrical parameter of the treadmill representative of the interaction between the user and the physical exercise surface detected by the data processing unit;

increasing the training speed of the physical exercise surface by the motor of the treadmill based on the variation of said at least a first electrical parameter of the treadmill representative of the interaction between the user and the physical exercise surface of the treadmill correlated with the action of the user on the physical exercise surface increasing the training speed of the physical exercise surface;

decreasing the training speed of the physical exercise surface by the motor of the treadmill based on the variation of said at least a first electrical parameter of the treadmill representative of the interaction between the user and the physical exercise surface of the treadmill correlated with the action of the user on the physical exercise surface decreasing the training speed of the physical exercise surface.

* * * * *